US006741353B1

(12) United States Patent
Johs

(10) Patent No.: US 6,741,353 B1
(45) Date of Patent: May 25, 2004

(54) SPECTROSCOPIC ELLIPSOMETRY ANALYSIS OF OBJECT COATINGS DURING DEPOSITION

(75) Inventor: Blaine D. Johs, Lincoln, NE (US)

(73) Assignee: J.A. Woollam Co., Inc., Lincoln, NE (US)

(*) Notice: Subject to any disclaimer, the term of this patent is extended or adjusted under 35 U.S.C. 154(b) by 66 days.

(21) Appl. No.: 10/199,536

(22) Filed: Jul. 19, 2002

Related U.S. Application Data
(60) Provisional application No. 60/306,545, filed on Jul. 20, 2001.

(51) Int. Cl.⁷ .............................. G01N 21/55; G01J 4/00
(52) U.S. Cl. ...................................... 356/445; 356/369
(58) Field of Search ................................. 356/630, 445, 356/369; 451/6; 118/712; 156/345.13, 345.17

(56) References Cited

U.S. PATENT DOCUMENTS

| 4,764,680 A | * | 8/1988 | Geary .......................... 356/513 |
| 4,841,778 A | * | 6/1989 | Butler et al. ................... 73/800 |
| 5,313,044 A | * | 5/1994 | Massoud et al. ........ 219/121.85 |
| 5,408,322 A | * | 4/1995 | Hsu et al. ..................... 356/369 |
| 5,665,241 A | * | 9/1997 | Maeda et al. ................ 210/683 |
| 5,871,805 A | | 2/1999 | Lemelson ....................... 427/8 |
| 6,081,334 A | * | 6/2000 | Grimbergen et al. ........ 356/369 |
| 6,141,103 A | * | 10/2000 | Pinaton et al. ............... 356/369 |
| 6,278,809 B1 | | 8/2001 | Johnson et al. ................ 385/12 |
| 6,630,995 B1 | * | 10/2003 | Hunter ..................... 356/237.5 |

* cited by examiner

Primary Examiner—Michael P. Safina
Assistant Examiner—Juan Valentin
(74) Attorney, Agent, or Firm—James D. Welch

(57) ABSTRACT

Disclosed is methodology for determination of parameters which characterize parameters such as thickness, color or quality of films deposited onto objects of arbitrary shapes, utilizing spectroscopic ellipsometry applied to standard shaped objects.

19 Claims, 3 Drawing Sheets

SPECTROSCOPIC ELLIPSOMETRY ANALYSIS OF OBJECT COATINGS DURING DEPOSITION

This Application Claims benefit from Provisional Application Serial No. 60/306,545 filed Jul. 20, 2001.

This invention was developed partitially with support from a Federal Grant. The United States Government might have certain rights to the invention claimed in this Patent.

TECHNICAL FIELD

The present invention relates to the determination of parameters which Identify properties of films, and more particularly to determination of parameters which characterize such as the thickness, color or quality of films deposited onto objects of arbitrary shapes, utilizing spectroscopic ellipsometry as applied to standard shaped objects.

BACKGROUND

Objects which are to be coated with a material for any purpose, (to effect color and/or to improve its functional surface properties etc.), are often of an arbitrary shape and are constantly translated and/or rotated during the deposition procedure to improve the uniformity of the deposition. Such motion can preclude positioning an ellipsometer system so that a beam of electromagnetic radiation provided thereby can constantly, or even periodically, predictably and reliably be directed into a detector.

With the invention disclosed herein in mind, a Patent Search for relevant art was conducted and provided very little. A Patent to Johnson et al. U.S. Pat. No. 6,278,809 was identified and describes provision of an optical fiber onto which is deposited materials. A combination of monochromatic and Broadband light transmitted through said optical fiber is affected by the deposition in a way which is detectable and determinative of factors such as real time growth rate and film composition, refractive index, thickness, surface roughness etc. U.S. Pat. No. 5,871,805 to Lemelson describes the use of a test blank in a deposition system which is monitored by an ellipsometer to provide information applicable in process control.

A need remains for a method of reliably monitoring and controlling the deposition of materials onto irregular shaped objects.

DISCLOSURE OF THE INVENTION

It is well known to deposit material films onto irregular shaped objects to change their color or surface properties etc., but real time quality control of such depositions remains difficult. Common practice is to simply follow a scheduled routine with little or no real time feedback, which routine typically works. The results of each such batch run are then evaluated after the fact. This can, and does, lead to entire batches of processed objects having to be disposed of, or recycled.

The disclosed invention comprises, in the context of material film deposition onto objects of arbitrary shape, the use of electromagnetic radiation to monitor test objects, which test objects present with other than substantially flat surfaces and typically, symmetry about at least one axis. Presently preferred, but non-limiting test object shapes include cylindrical and spherical. In use a beam of electromagnetism is caused to Interact therewith and enter a detector during a deposition procedure. In use the said test object is placed near to the actual object during a deposition procedure and typically is caused to undergo a similar motion to that of the actual object.

Further, it is specifically noted that one or more such test objects can be affixed to a planetary motion system which periodically positions each of the test objects in the path of the electromagnetic beam such that said electromagnetic beam reflects therefrom and then predictably enters into a detector. It is specifically pointed out that such test objects can be made to spin about an axis of its symmetry to simulate the motion of actual objects under process.

A disclosed method of monitoring the results of material deposition onto objects then comprises the steps of:

a. providing a material deposition system including means for causing a beam of electromagnetic radiation to interact with and reflect from an other than substantially flat surface of an object placed therewithin and enter a detector;

b. placing objects onto which material is to be deposited into said material deposition system, including at least one test object which demonstrates at least one axis of symmetry;

c. optionally causing said at least one test object to rotate about at least one axis of symmetry thereof;

d. causing the material deposition system to deposit material onto the objects and at least one test object; and e. causing electromagnetic radiation to interact with and reflect from said other than substantially flat surface of said test object, and enter the detector.

Steps d. and e. are beneficially practiced simultaneously.

A variation of the described method provides that more than one test object be placed on a means for sequentially placing them into the path of said beam of electromagnetic radiation, and that said more than one test objects be sequentially entered into the ellipsometric beam.

The at least one test object is preferably of a shape selected from the group consisting of:

cylindrical; and spherical.

The method of monitoring the results of material deposition onto objects is especially applicable to control of the deposition of material which is appropriate to alter a selection from the group consisting of:

color; and mechanical properties.

The detector which is positioned to receive the ellipsometric electromagnetic beam outputs information which is used to control the deposition process.

While not limiting, it is noted that the preferred source of electromagnetic radiation which is caused to interact with and reflect from a test object, is an ellipsometer system which is sequentially comprised of, prio to said Test Object a Polarization State Generator comprising:

a polychromatic source of electromagnetic radiation;

a polarizer;

optionally a compensator and a Polarization State Detector after said test object comprising:

optionally a compensator;

an analyzer; and a multiple element detector system positioned to intercept reflected electromagnetic radiation after said test object.

It is also noted that most ellipsometry is practiced by causing electromagnetic radiation to interact with and reflect from a substrate which has a substantially flat surface. The disclosed invention herein causes electromagnetic radiation to reflect from a test object surface which is other than substantially flat.

The disclosed invention will be better understood by reference to the Detailed Description Section of this Specification, in conjunction with the drawings.

BRIEF DESCRIPTION OF THE DRAWINGS

FIG. 1b shows a cross-sectional taken at a—a in FIG. 1a.

FIG. 1d shows a cross-sectional taken at c—c in FIG. 1a.

DETAILED DESCRIPTION

Figure 1A:
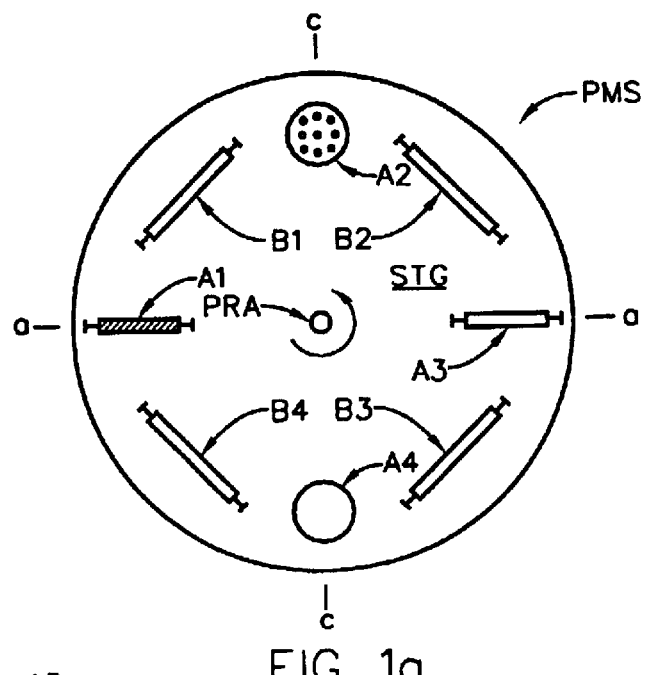
FIG. 1a shows Symmetrical Test Object containing Planetary Motion System (PMS) which in use is placed into a Deposition System and caused to rotate about the Planetary Rotation Axis (PRA).
Figure 1B:
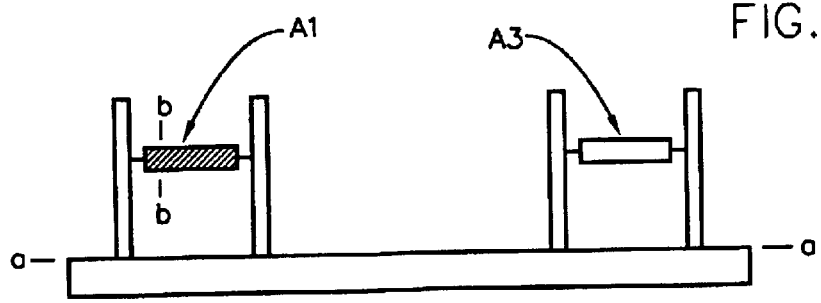
Figure 1C:
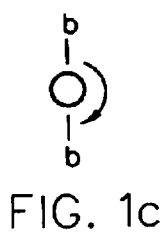
FIG. 1c shows a cross-sectional taken at b—b in FIG. 1b.
Figure 1D:
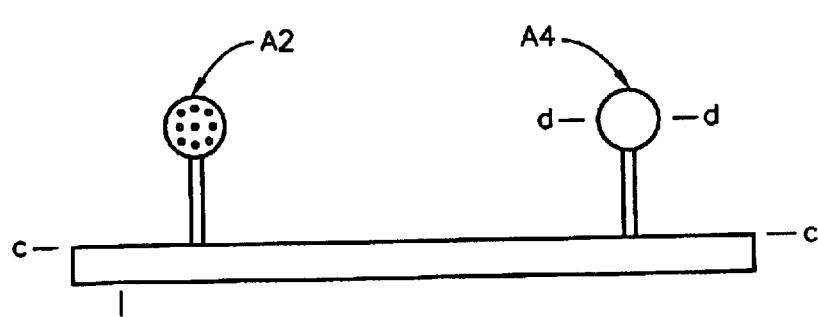
Figure 1E:
FIG. 1e shows a cross-sectional taken at d—d in FIG. 1d.

FIG. 1a shows a Symmetrical Test Object containing Planetary Motion System (PMS) which in use is placed into a Deposition System and caused to rotate about the Planetary Rotation Axis (PRA). At least some of the shown objects A1, A2 A3, A4, B1, B2, B3 and B4 are mounted so as to be rotatable about an axis such as identified by reference to FIGS. 1b and 1c, which show cross-sectionals with respect to Object A1. FIGS. 1d and 1e similarly demonstrate rotation with respect to Object A4. That is, while the Planetary Motion Stage (PMS) Stage (STG) is caused to rotate about about Planetary Rotation Axis (PRA), Objects on Stage (STG) can be made to rotate about axes of symetry thereof, much as planets orbit around the sun, and rotate about an axis.

Object A1 can be interpreted to be a worm gear to which a coating is to be applied, while Object A3 presents a smooth surface cylindrical shaped Test Object of similar dimensions to said worm gear. Object A2 can be interpreted to represent a substantially spherical object with dimples present in the surface thereof, which Object A4 can be interpreted to be a spherical shaped Test Object with a smooth surface. Objects B1, B2, B3 and B4 can be interpreted as general representations of Objects which can be of any shape and/or surface characteristics, and positioned other than along radial projections. Objects can be oriented on the Stage (STG) in any functional manner.

It is important to note that while most ellipsometry is performed on substantially flat substrate surfaces, the disclosed invention teaches use of beams of electromagnetic radiation to investigate smooth curved surfaces, such as presented by cylinders, (eg. Object A3), and spheres, (eg. Object A4).

Figure 2A:
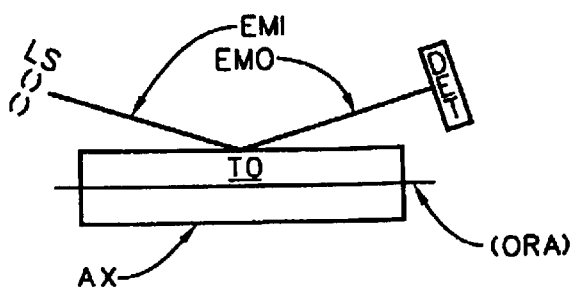
FIGS. 2a and 3a demonstrate that a Source of Electromagnetic Radiation (LS) can be positioned to provide a beam of electromagnetic radiation such that it reflects from at least one Test Object (TO) (eg. (Ax) and/or (BX)), and enters a Detector (DET).
Figure 3A:
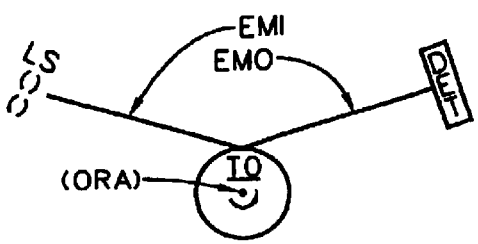
Figure 2B:
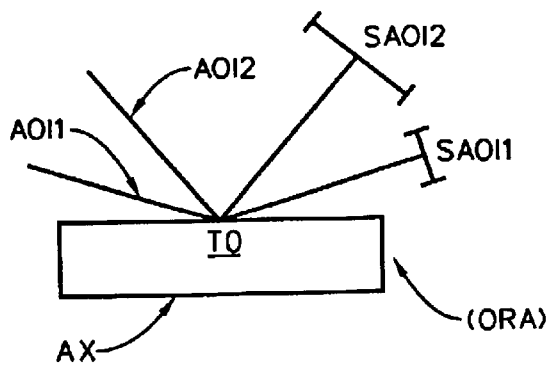
FIGS. 2b and 3b show how the Angle-Of-Incidence (AOI) change affects electromagnetic beam spreads (SAOI1 & SAOI2) at a Detector depends on the orientation of the demonstrate cylindrical test object (TO).
Figure 3B:
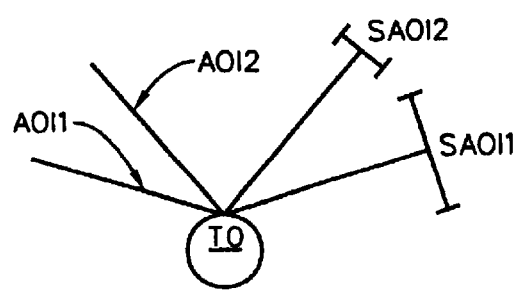

FIGS. 2a and 3a demonstrate that a Source of Electromagnetic Radiation (LS) can be positioned to provide a beam of electromagnetic radiation such that it reflects from at least one Test Object (TO), and enters a Detector (DET). FIGS. 2b and 3b show how the Angle-Of-Incidence (AOI) change affects electromagnetic beam spreads (SAOI1 & SAOI2) at a Detector depends on the orientation of the demonstrate cylindrical test object (TO). The spreads (SAOI1 & SAOI2), while decreasing intensity, provides for easier interception by a Detector. It should be appreciated that the FIG. 1a configuration allows sequentially placing a plurality of test objects into the pathway of the electromagnetic beam during a deposition procedure by rotation around Planetary Rotation Axis (PRA).

It should be understood that the purpose of monitoring material deposition onto the other than substantially flat surface a test object (TO) is to allow monitoring of material deposition onto actual fabrication objects which are of arbitrary shapes, and which therefore do not allow investigation by an electromagnetic beam caused to Impinge thereupon, as the reflected beam direction can not be easily controlled and caused to enter a detector. For instance, with reference to FIG. 1a, investigation of gear or dimpled sphere Objects A1 or A2 will not provide well behaved reflections from their surfaces, while investigation of Test objects A3 or A4 will provide much better behaved and predictable results.

Figure 4:
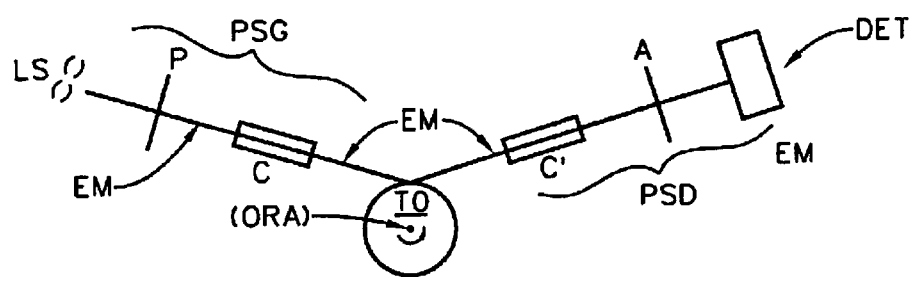
FIG. 4 demonstrates an ellipsometer system comprised of a Source of Electromagnetic Radiation (LS), a Polarizer (P), optional Compensators (C) (C'), an Analyzer (A) and a Detector, (to be understood as comprising multiple detector elements).

FIG. 4 demonstrates an ellipsometer system comprised of a Source of Electromagnetic Radiation (LS), a Polarizer (P), optional Compensators (C) (C'), an Analyzer (A) and a Detector, (to be understood as comprising multiple detector elements). It is important to note that the Beam of Electromagnetic Radiation (EM) reflects from a Test Object (TO) which has a surface other than substantially flat. It is noted that ellipsometry is typically practiced to investigate a substantially flat surface of a substrate and application of the technique as described herein is believed to be novel.

Figure 5:
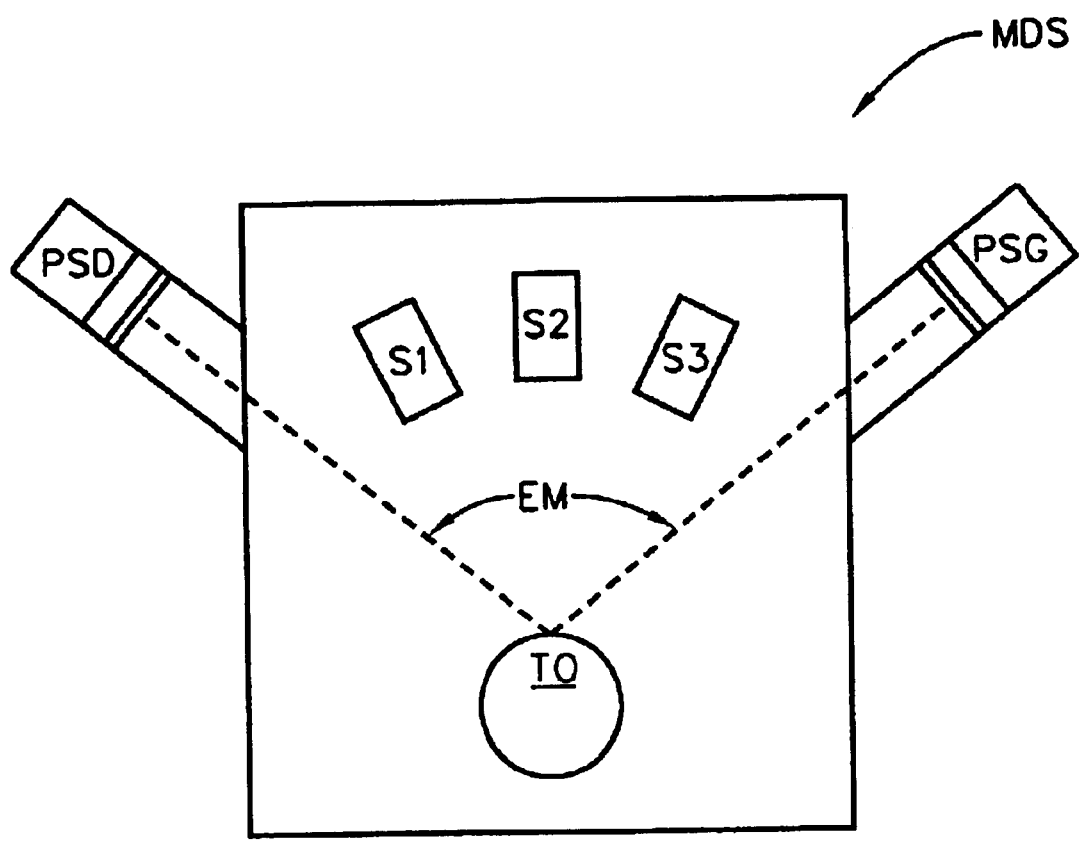
FIG. 5 demonstrates a Material Deposition System (MDS).

FIG. 5 demonstrates a Material Deposition System (MDS) including three (S1) (S2) (S3) sources of materials to be deposited onto objects. Typically vacuum pump capability will also be present, (not shown), to control the pressure therein. 10 Note the presence of the Polarization State Generator (PSG) and Polarization State Detector (PSD) as identified in FIG. 4, as well as the Test Object (TO), (which could be, for instance, Object A3 or A4 on the Planetary Motion System (PMS) in FIG. 1a).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of monitoring the results of material deposition onto objects comprising the steps of:

a) providing a material deposition system including means for causing a beam of electromagnetic radiation to interact with and reflect from a surface of an object placed there within, then enter a detector;

b) placing a plurality of objects onto which material is to be deposited into said material deposition system, including at least one test object having a surface which is other than substantially flat;

c) optionally causing said at least one test object to rotate about at least one axis;

d) causing the material deposition system to deposit material onto the objects including said at least one test object; and e) causing electromagnetic radiation to interact with and reflect from the other than substantially flat surface of said test object, and enter the detector.

2. A method of monitoring the results of material deposition onto objects as in claim 1, in which steps d) and e) are practiced simultaneously.

3. A method of monitoring the results of material deposition onto objects as in claim 1, in which more than one test object is present on a means for sequentially placing them into the path of said beam of electromagnetic radiation.

4. A method of monitoring the results of material deposition onto objects as in claim 2, in which more than one test object is present on a means for sequentially placing them into the path of said beam of electromagnetic radiation.

5. A method of monitoring the results of material deposition onto objects as in claim 1, in which the shape of at least one test object is selected from the group consisting of:
   cylindrical; and
   spherical.

6. A method of monitoring the results of material deposition onto objects as in claim 2, in which the shape of at least one test object is selected from the group consisting of:
   cylindrical; and
   spherical.

7. A method of monitoring the results of material deposition onto objects as in claim 3, in which the shape of at least one test object is selected from the group consisting of:
   cylindrical; and
   spherical.

8. A method of monitoring the results of material deposition onto objects as in claim 1, in which the material deposited is appropriate to alter a selection from the group consisting of:
   color; and
   mechanical;
properties.

9. A method of monitoring the results of material deposition onto objects as in claim 2, in which the material deposited is appropriate to alter a selection from the group consisting of:
   color; and
   mechanical;
properties.

10. A method of monitoring the results of material deposition onto objects as in claim 3, in which the material deposited is appropriate to alter a selection from the group consisting of:
    color; and
    mechanical;
properties.

11. A method of monitoring the results of material deposition onto objects as in claim 4, in which the material deposited is appropriate to alter a selection from the group consisting of:
    color; and
    mechanical;
properties.

12. A method of monitoring the results of material deposition onto objects as in claim 1, in which the detector outputs information which is used to control the deposition process.

13. A method of monitoring the results of material deposition onto objects as in claim 2, in which the detector outputs information which is used to control the deposition process.

14. A method of monitoring the results of material deposition onto objects as in claim 1, in which causing electromagnetic radiation to interact with and reflect from a test object and enter the detector involves reflection from a surface which is other than substantially flat.

15. A method of monitoring the results of material deposition onto objects as in claim 1, in which causing electromagnetic radiation to interact with and reflect from a test object and enter the detector involves use of an ellipsometer which is sequentially comprised of a source of electromagnetic radiation, a polarizer and optionally a compensator prior to said test object, and optionally a compensator, an analyzer and multiple element detector system positioned to intercept reflected electromagnetic radiation from said test object.

16. A method of monitoring the results of material deposition onto objects comprising the steps of:

a) providing a material deposition system including ellipsometer means for causing a beam of electromagnetic radiation to interact with and reflect from an other than substantially flat surface of an object placed there within, and thereafter enter a detector, said ellipsometer sequentially comprising a source of electromagnetic radiation, a polarizer, optionally a compensator, said other than substantially flat surface of said object, optionally a compensator, an analyzer and said detector which is comprised of multiple detector elements;

b) placing a plurality of objects with other than substantially flat surfaces onto which material is to be deposited into said material deposition system, including at least one test object;

c) optionally causing said at least one test object to rotate;

d) causing the material deposition system to deposit material onto the objects including said at least one test object; and e) causing electromagnetic radiation to pass through said polarizer, interact with and reflect from an other than substantially flat surface of said at least one test object, pass through said analyzer and enter the detector.

17. A method of monitoring the results of material deposition onto objects as in claim 16, in which steps d) and e) are practiced simultaneously.

18. A method of monitoring the results of material deposition onto objects as in claim 16, in which the material deposited is appropriate to alter a selection from the group consisting of:
    color; and
    mechanical;
properties.

19. A method of monitoring the results of material deposition onto objects as in claim 16, in which the shape of at least one test object is selected from the group consisting of:
    cylindrical; and
    spherical.

* * * * *